(12) United States Patent
Luce

(10) Patent No.: US 6,679,842 B2
(45) Date of Patent: Jan. 20, 2004

(54) TONOMETER CALIBRATION TOOL

(75) Inventor: David A. Luce, Clarence Center, NY (US)

(73) Assignee: Reichert, Inc., Depew, NY (US)

(*) Notice: Subject to any disclaimer, the term of this patent is extended or adjusted under 35 U.S.C. 154(b) by 81 days.

(21) Appl. No.: 10/122,807

(22) Filed: Apr. 15, 2002

(65) Prior Publication Data

US 2003/0195430 A1 Oct. 16, 2003

(51) Int. Cl.[7] .................................................. A61B 3/16
(52) U.S. Cl. ........................ 600/398; 600/401; 73/1.01
(58) Field of Search ................................. 600/398, 399, 600/401, 405, 558, 561, 587; 351/200, 205, 208; 73/1.01, 1.05, 1.16, 1.57

(56) References Cited

U.S. PATENT DOCUMENTS

| | | | | |
|---|---|---|---|---|
| 4,220,038 A | * | 9/1980 | Kantorski | 73/1.08 |
| 4,834,105 A | * | 5/1989 | Matthews et al. | 600/401 |
| 5,474,066 A | * | 12/1995 | Grolman | 600/398 |
| 5,868,580 A | * | 2/1999 | Amrein et al. | 434/271 |
| 6,419,631 B1 | * | 7/2002 | Luce | 600/401 |

FOREIGN PATENT DOCUMENTS

JP   11-225974   8/1999

OTHER PUBLICATIONS

Physikalisch–Technische Bundesanstalt (PTB); "Testing of eye tonometer"; web page http://www.berlin.ptb.de/8/82/822/822augen_en.html.

* cited by examiner

Primary Examiner—Charles Marmor
(74) Attorney, Agent, or Firm—Hodgson Russ LLP

(57) ABSTRACT

An apparatus for calibrating a non-contact tonometer comprises an electronic eye having a damped pressure sensor for receiving a tonometer air pulse and providing a pressure signal in response to the air pulse, and an applanation simulator connected to the pressure sensor for providing a pseudo-applanation event when the pressure signal reaches a predetermined level corresponding to a known IOP measurement standard. A method for calibrating a non-contact tonometer using the inventive calibration apparatus is also described.

32 Claims, 9 Drawing Sheets

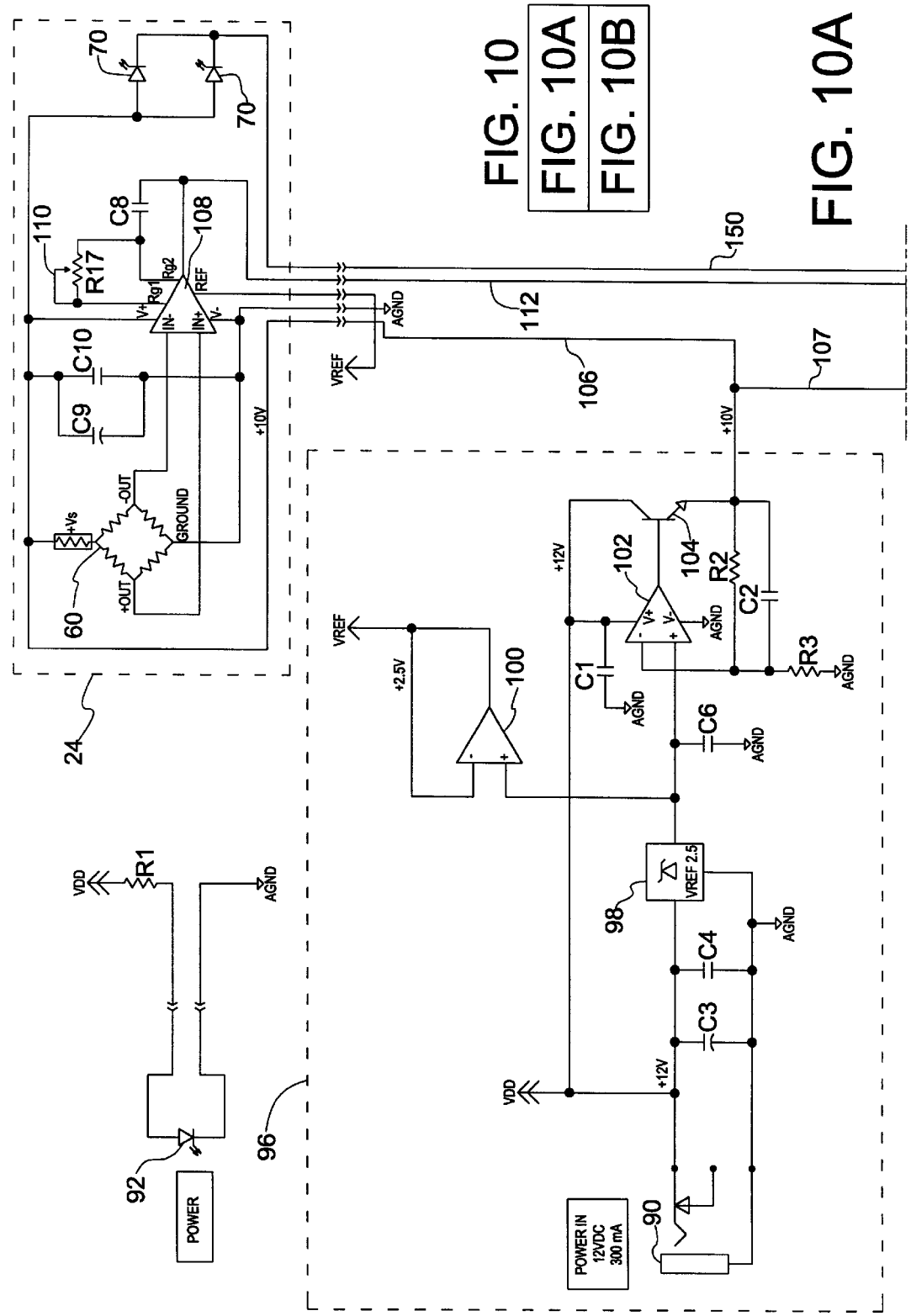

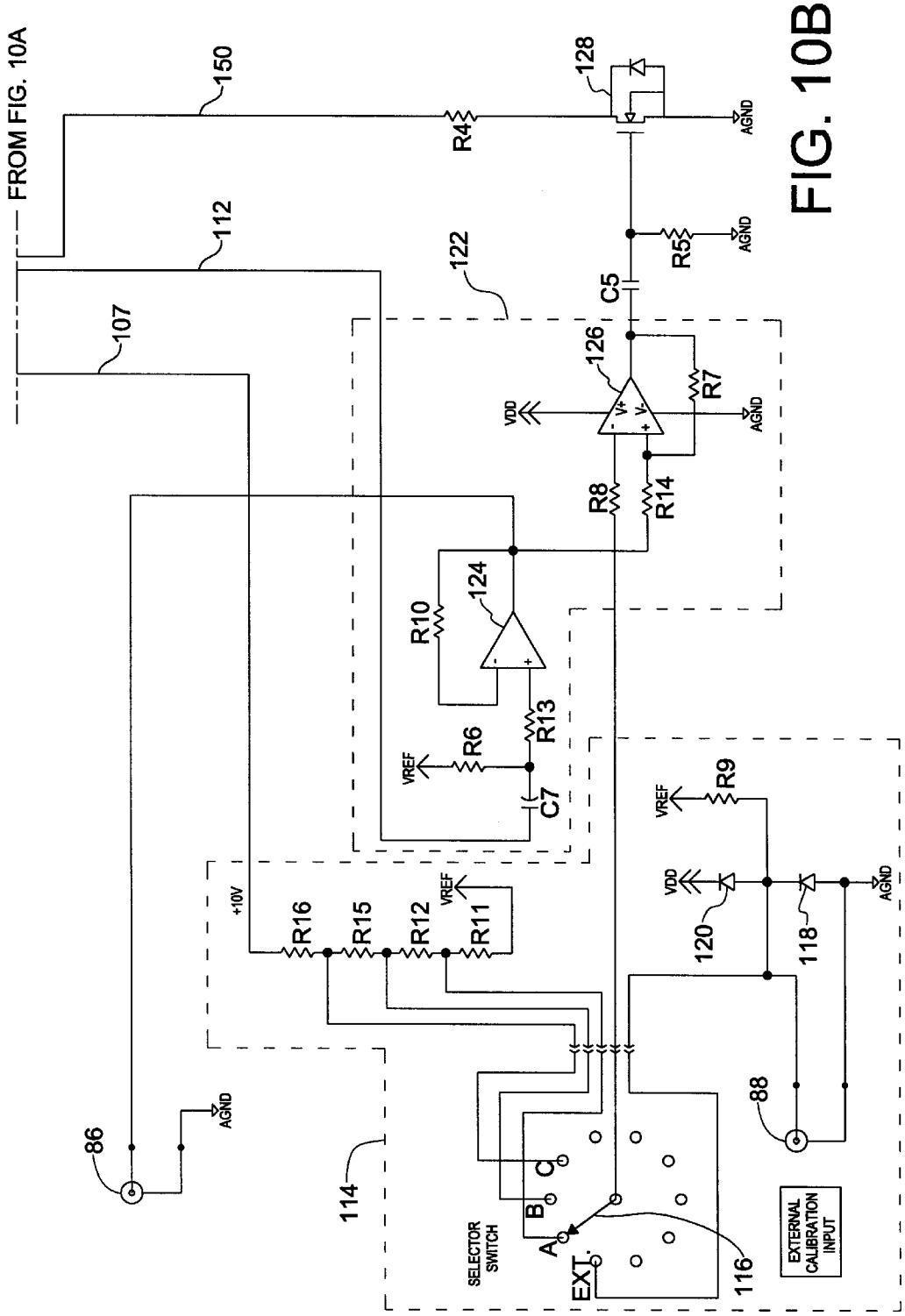

TONOMETER CALIBRATION TOOL

FIELD OF THE INVENTION

The present invention relates generally to ophthalmic non-contact tonometers of a type operable to discharge an air pulse at an eye to applanate an area of the cornea for measuring intraocular pressure (IOP), and relates more specifically to a calibration apparatus and method for non-contact tonometers of the stated type.

BACKGROUND OF THE INVENTION

Existing non-contact tonometers measure IOP by activating a pump mechanism to fire an air pulse at the cornea to flatten or "applanate" a predetermined area of the cornea, detecting corneal applanation caused by the air pulse and a plenum pressure of the pump mechanism, and correlating the plenum pressure at the moment of applanation with IOP. In older instruments, the time elapsed to achieve applanation was correlated to IOP as an "indirect" representation of plenum pressure based on a linearly increasing pressure profile in the plenum. In present day instruments, a pressure sensor is mounted in the plenum for providing a signal proportional to the plenum pressure. Regardless of whether elapsed time or a signal from a pressure sensor is obtained, it is necessary to correlate the obtained quantity to IOP such that the instrument provides a meaningful measurement value of IOP as output. Thus, non-contact tonometers must be calibrated periodically to ensure that the correlation function used by the particular instrument yields IOP results that are substantially in agreement with an established standard of IOP measurement.

Traditionally, the Goldmann applanation tonometer (GAT), which measures IOP by directly contacting the cornea to applanate an area of the cornea, has been used as a standard for IOP measurement. Accordingly, initial calibration of a non-contact tonometer has been carried out by way of a clinical trial involving a large number of human eyes. During the clinical trial, each eye is measured with both GAT and the subject non-contact tonometer, and the parameters of a correlation function of the subject non-contact tonometer are adjusted to provide a best fit to the GAT results.

Conducting clinical trials is time consuming and expensive, and therefore clinical calibration might be conducted with respect to a "master" non-contact tonometer, and the master non-contact tonometer is then used as a calibration standard. It is known to measure "IOP" of a set of precision-manufactured rubber eyes designed and tested to applanate at predetermined pressures as a calibration gauge to avoid a clinical trial involving human eyes. Rubber eyes develop folds during testing and tend to be a poor simulation of a real eye. Moreover, rubber eyes are expensive and difficult to manufacture because very tight tolerances are necessary. Finally, the rubber material ages or can be damaged, so that a set of rubber eyes must be constantly recalibrated to maintain reliability.

The Physikalisch-Technische Bundesanstalt (PTB) of Germany has developed a calibration tool for non-contact tonometers that employs a mirror and lever system, wherein the tonometer air pulse is directed at a mirror mounted on a lever to angularly displace the lever about a pivot axis. A working version of the tool incorporates a complex assembly of precision moving parts and is available at a cost of close to $30,000.00.

Finally, Japanese Patent No. 11-225974 describes another mechanical calibration tool generally similar in concept to the PTB calibration tool in that it comprises a mirror mounted for measurable deflection by a tonometer air pulse.

Thus, tonometer calibration devices and methods of the prior art are delicate, expensive, unstable, and/or difficult to use, and they cannot be traced to an absolute pressure standard such as that provided by a water column or precision pressure calibrator.

SUMMARY OF THE INVENTION

Therefore, it is an object of the present invention to provide an apparatus for calibrating a non-contact tonometer that is inexpensive and reliable over time.

It is another object of the present invention to provide an apparatus for calibrating a non-contact tonometer that is easy to operate.

It is another object of the present invention to provide an apparatus for calibrating a non-contact tonometer that is traceable to an absolute pressure standard.

It is a further object of the present invention to provide a tool and method for calibrating a non-contact tonometer that minimizes influence of an operator's skill level.

An apparatus of the present invention for calibrating a non-contact tonometer comprises a calibration tool mountable in front of an air tube of a non-contact tonometer. The calibration tool includes "an electronic eye" having a pressure sensor for receiving the air pulse and applanation simulation means connected to the pressure sensor for providing a pseudo-applanation event, such as an infra-red pulse, when the pressure sensor signal reaches a predetermined level. The pressure sensor includes a piezoresistive semiconductor sensing element covered by a polymer gel for reducing flow noise in the sensor signal. In addition to the electronic eye, the calibration tool preferably includes a glass sphere for use in aligning the non-contact tonometer, a planar mirror for use in setting proper angular orientation of the calibration tool about X and Y axes of the system, and a rubber eye for use in conducting a known "fire around" offset test. The electronic eye, glass eye, mirror, and rubber eye are carried on a precision slide mechanism making it easy to manually slide a new station into position in front of the tonometer air tube.

The calibration apparatus further comprises a controller unit in a housing remote from the calibration tool mounted in front of the tonometer. The controller enables adjustment of the threshold pressure signal voltage between settings corresponding to low, medium, and high IOP calibration values. The controller also allows for input of a signal from an external calibration device.

The invention also encompasses a method of calibrating a non-contact tonometer using the tonometer calibration apparatus. The method preferably comprises the steps of operating the non-contact tonometer to direct an air pulse onto a pressure sensor; comparing a pressure signal from the pressure sensor with a predetermined signal level corresponding to a known IOP measurement standard; inducing the non-contact tonometer to detect applanation when the pressure signal from the pressure sensor reaches the predetermined signal level such that the non-contact tonometer provides a measured pressure value; repeating the aforementioned steps for other known IOP measurement standards; and adjusting at least one parameter of a correlation function of the non-contact tonometer to reduce a difference between the measured pressure values and the known IOP measurement standards.

BRIEF DESCRIPTION OF THE DRAWING

The nature and mode of operation of the present invention will now be more fully described in the following detailed description of the invention taken with the accompanying drawing figures, in which:

FIGS. 10A and 10B, collectively referred to as FIG. 10, form an electrical schematic diagram of the controller and an associated pressure sensor of the tonometer calibration tool;

DETAILED DESCRIPTION OF THE INVENTION

Figure 1:
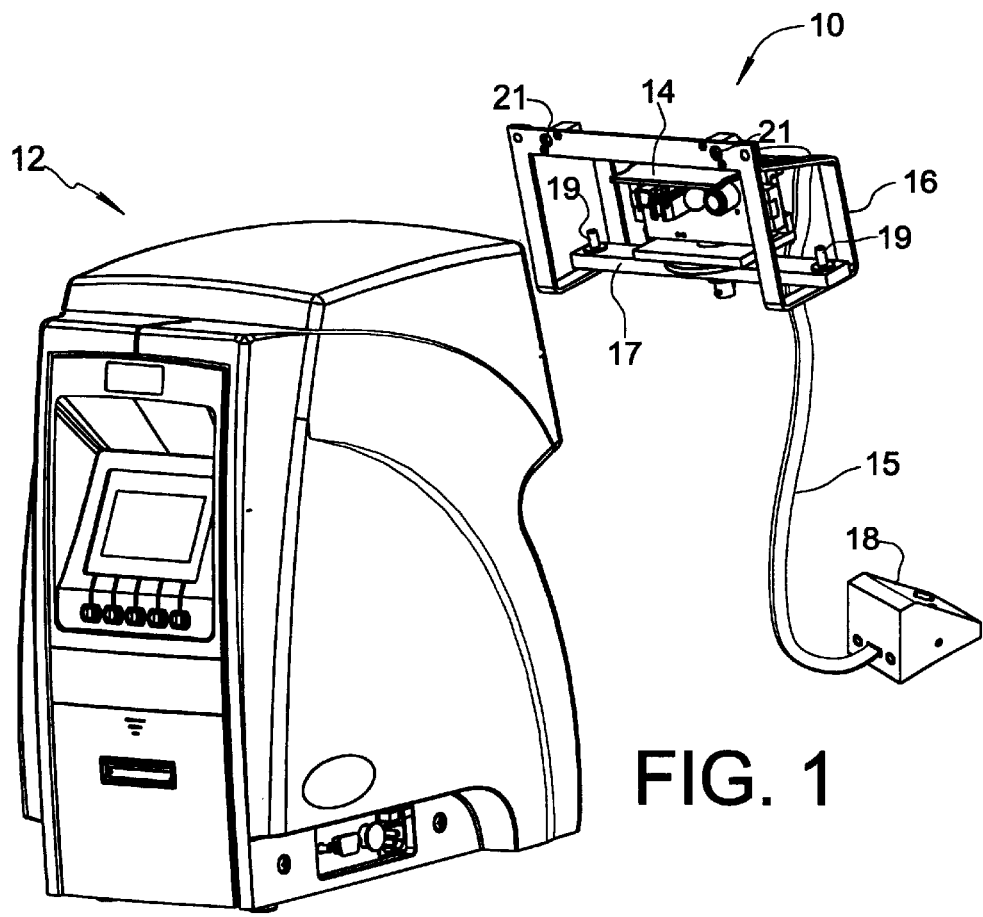
FIG. 1 is a perspective view of a tonometer calibration system formed in accordance with a preferred embodiment of the present invention.
Figure 2:
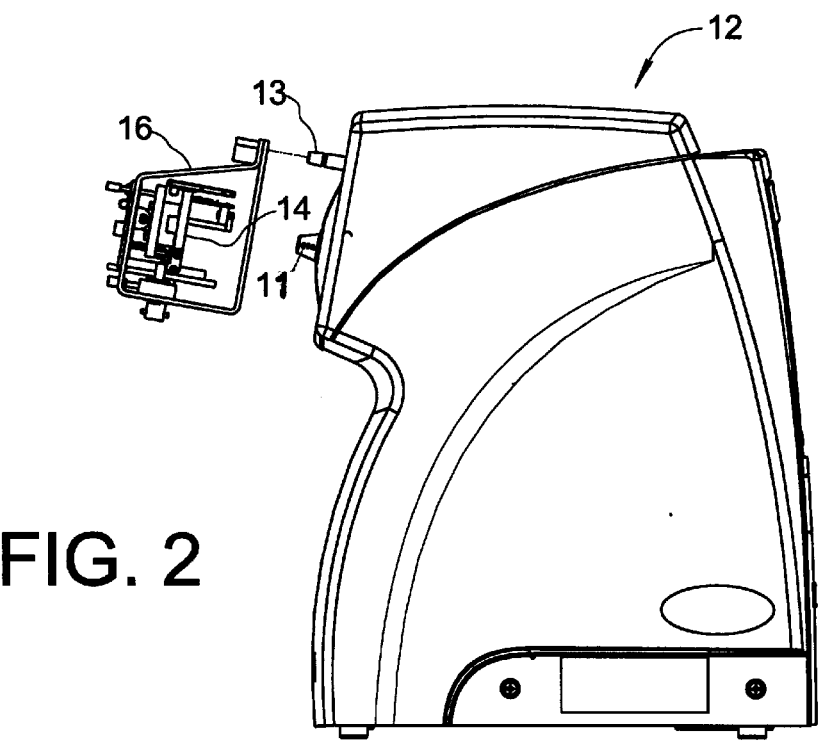
FIG. 2 is a side elevational view showing an arrangement for mounting a tonometer calibration tool of the present invention on a non-contact tonometer in accordance with the calibration system shown in FIG. 1.
Figure 3:
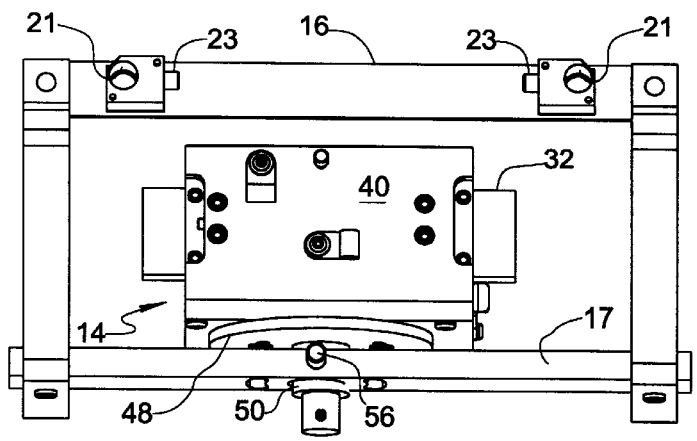
FIG. 3 is a rear elevational view of the tonometer calibration tool and a hanging fixture therefor.

FIG. 1 shows a calibration system 10 of the present invention. Calibration system 10 generally includes a non-contact tonometer (NCT) 12, a tonometer calibration tool 14 positioned opposite a test portion of NCT 12 by a fixture 16, and a controller 18 connected to tonometer calibration tool 14. Referring also now to FIGS. 2 and 3, tonometer calibration tool 14 includes a swivel platform 48 having a swivel shaft 50 received through a central opening in a transverse support bracket 17 which bridges fixture 16 and is releasably clamped to fixture 16 by fasteners 19 at each opposite end. Fixture 16 includes a pair of transversely spaced upper mounting holes 21 for receiving corresponding support pegs 13 protruding from the front of NCT 12 to locate tonometer calibration tool 14 in front of an air discharge tube 11 of NCT 12. The height of tonometer calibration tool 14 relative to support bracket 17 is adjustable using a rear set screw 56.

Figure 4:
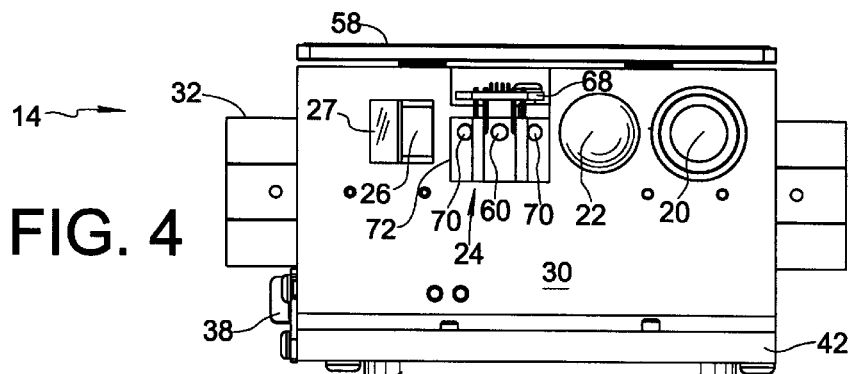
FIG. 4 is a front elevational view of the tonometer calibration tool shown in FIG. 2.
Figure 5:
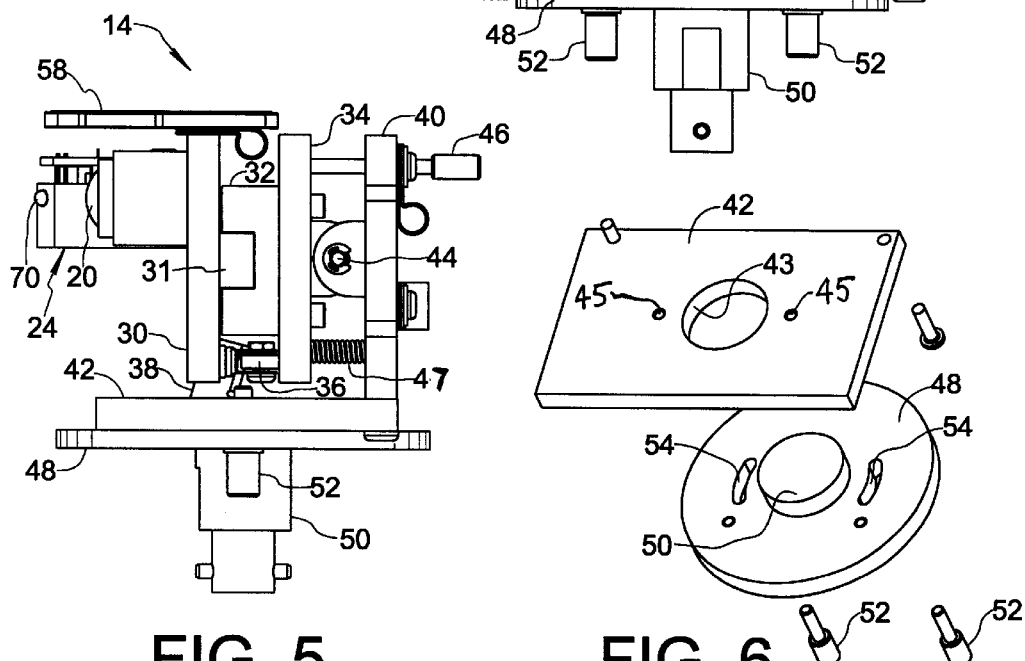
FIG. 5 is a side elevational view of the tonometer calibration tool shown in FIG. 2.

Referring now to FIG. 4, it can be seen that calibration tool 14 preferably comprises four stations including a rubber eye 20, a reflective glass sphere 22, an "electronic eye" 24, and a planar mirror 26 behind an attenuating filter 27. The various stations of calibration tool 14 are mounted on an upstanding front plate 30, which in turn is fixed to a horizontal slider 31 of a precision linear slide mechanism. Slider 31 moves in a slider track 32 to permit manual adjustment of front plate 30 along an X-axis of the system (left-right in FIG. 4). Slider track 32 is fixed to an upstanding middle plate 34 arranged parallel to front plate 30, and a stabilizer wheel 36 is fixed to a rear surface of front plate 30 and contacts a front surface of middle plate 34. The coupling of slider 31 within slider track 32 is characterized by a series of precisely spaced detent stops (not shown) respectively corresponding to rubber eye 20, glass sphere 22, electronic eye 24, and planar mirror 26, whereby a chosen station can be manually located in front of NCT air tube 11 by shifting the slide mechanism.

Figure 6:
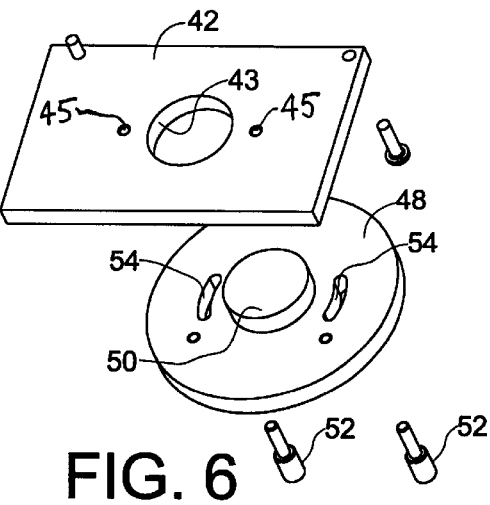
FIG. 6 is an exploded perspective view showing a swivel mount of the tonometer calibration tool.

Middle plate 34 is coupled to a parallel upstanding rear plate 40 by a pivot connection 44 defining a tilt axis for the middle plate, slider mechanism, and front plate. Rear plate 40 is fixed to a base plate 42, and a tilt adjustment screw extends through the rear plate and is operatively connected to middle plate 34 for adjusting a tilt angle of the middle plate about the tilt axis of pivot connection 44, whereby the angular tilt (gamma angular adjustment) of middle plate 34 relative to base plate 42 can be set. Base plate 42 is supported by swivel platform 48 and, as seen in FIG. 6, includes an opening 43 receiving swivel shaft 50. A pair of swivel set screws 52 extend through respective arcuate slots 54 in swivel platform 48 about the axis of swivel shaft 50 to mate with tapped holes 45 in base plate 42. As a result, an angular swivel orientation (theta angular adjustment) of base plate 42 relative to swivel platform 48 can be releasably set using swivel set screws 52. Thus, it is possible to adjust the angular orientation of electronic eye 24 about orthogonal axes defined by the pivot connection 44 and the swivel shaft 50.

Figure 7:
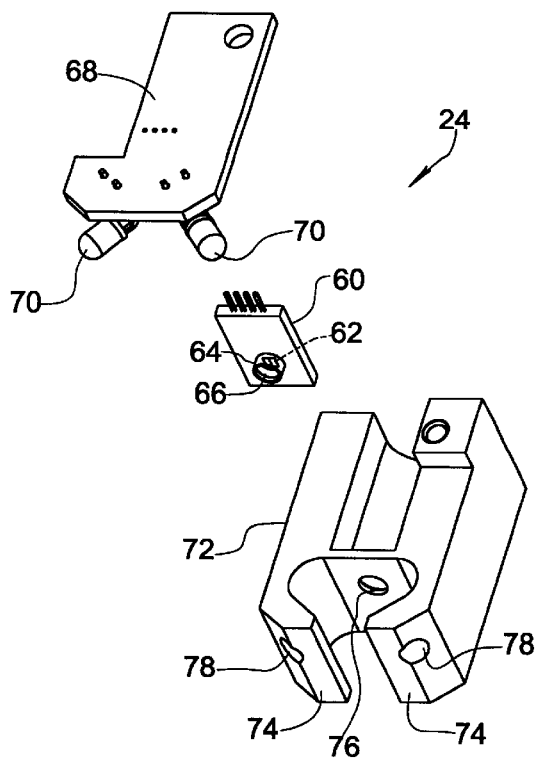
FIG. 7 is an enlarged perspective view of an electronic eye of the tonometer calibration tool.

Attention is now directed to FIG. 7 of the drawings, which shows electronic eye 24 in exploded view. In accordance with a currently preferred embodiment of the present invention, electronic eye 24 is an assembly comprising a unitary holder 72, a pressure sensor 60, a printed circuit board 68 associated with pressure sensor 60, and a pair of radiation emitters 70 also connected to printed circuit board 68. Holder 72 is configured to provide a pair of forwardly protruding angled arms 74 symmetrically spaced on opposite sides of a sensing element 62 of pressure sensor 60. Each arm 74 includes a directional hole 78 for receiving an emitter 70 such that radiation from each emitter 70 travels outward along respective axes which intersect back at a central location on the surface of sensing element 62. While two emitters 70 are shown, one emitter will suffice if it is positioned to direct radiation in the proper direction, which depends upon the detection system of NCT 12 and varies from NCT model to NCT model. Pressure sensor 60 is preferably of a type having a piezoresistive semiconductor sensing element covered by a polymer gel 66 that has a low Durometer hardness and acts to reduce flow noise in the generated pressure signal when pressure is applied to the sensing element by an air pulse. The polymer gel 66 is contained within a cylindrical well 64 leading to sensing element 62, and cylindrical well 64 is accommodated by a hole 76 provided in holder 72. A suitable pressure sensor for practicing the present invention is a chip pak high volume pressure sensor manufactured by Motorola, Inc. under part number MPX2300DT1. Pressure sensor 60 and emitters 70 are connected to printed circuit board 68, which includes a potentiometer 110 (see FIG. 10A) as will be described hereinafter.

Figure 8:
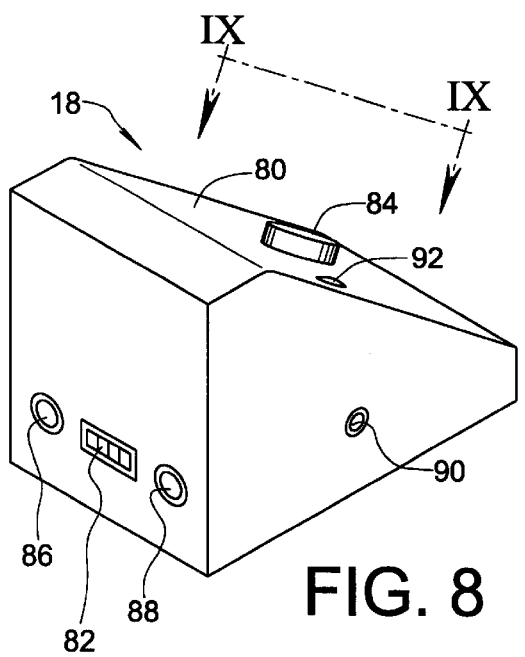
FIG. 8 is an isometric view of a controller for the tonometer calibration tool.
Figure 9:
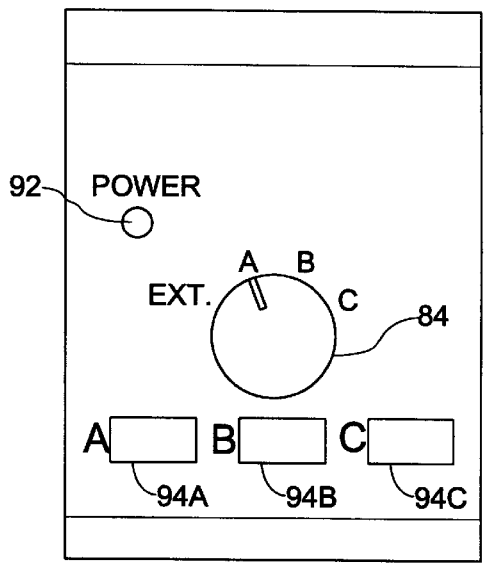
FIG. 9 is a view taken generally along the line IX—IX in FIG. 8.

As shown in FIG. 1, electronic eye 24 is connected to a remotely located controller 18 by an electrical cable 15 coupled to printed circuit board 68. Referring also now to FIGS. 8 and 9, controller 18 is depicted as being a separately-housed control unit comprising a housing 80 for enclosing a main controller circuit board (not shown), an externally accessible selector knob 84, a connection port 82 for receiving electrical cable 15, an input jack 88 for connecting an external calibration device, an output jack 86 for connecting an oscilloscope or other signal monitor, a power jack 90 for connecting a source of DC power such as an AC to DC adapter plugged into an AC wall outlet, and an LED 92 to indicate a "power on" condition when illuminated. As seen in FIG. 9, selector knob 84 is adjustable to four different positions, namely an external calibration position "EXT.", an "A" position, a "B" position, and a "C" position. Controller housing 80 preferably includes spaces 94A, 94B, and 94C for entering calibration IOP values corresponding to knob positions A through C.

FIGS. 10 is a schematic diagram of the electronic circuitry of controller 18 and electronic eye 24. The controller includes a power supply circuit 96 connected to power jack 90. Power supply circuit 96 utilizes a 2.5 volt precision bandgap reference 98 (Linear Technology Part No. LT1460-2.5), a pair of operational amplifiers 100 and 102 (both Analog Devices Part No. OP213ES), and a transistor 104 (Motorola Part No. MMBT3904LT1).

Power supply circuit 96 provides power to electronic eye 24 along line 106. As can be seen in FIG. 10A, the positive and negative voltage outputs from pressure sensor 60 are input to an instrumentation amplifier 108 (Analog Devices Part No. AMP04FS) connected to a potentiometer 110 for adjustably setting the gain of the amplifier. The output voltage signal from instrumentation amplifier 108 is in the form of an increasing pressure "ramp" signal when pressure sensor 60 is actuated by an air pulse, and is carried on line 112. Emitters 70 are also shown in FIG. 10A as being part of electronic eye 24. Emitters 70 are preferably infra-red light-emitting diodes (Panasonic Part No. LN68) chosen to communicate with applanation detectors intended to detect infra-red radiation, such as those currently employed in various non-contact tonometer models manufactured by Reichert Ophthalmic Instruments. Nevertheless, the nature of emitters 70 will depend upon the type of applanation detection system employed by NCT 12.

Controller 18 further includes a selector circuit 114 (FIG. 10B) having a selector switch 116 operable by a user through corresponding selector knob 84. In the present embodiment, selector circuit 114 provides three possible precision reference voltages respectively corresponding to switch positions A, B, and C, as well as an additional external calibration voltage corresponding to switch position "EXT CAL" that depends on an input signal received from an external device connected to input jack 88. Diodes 118 and 120 (both Philips Semiconductors Part No. PMLL4148) are high-speed switching diodes.

The chosen reference voltage signal from selector circuit 114 and the pressure voltage signal from instrumentation amplifier 108 are provided as inputs to a comparator circuit 122. The pressure voltage signal is fed through a buffer operational amplifier 124 (Analog Devices Part No. OP213ES), and the resulting signal is directed to the positive input of an operational amplifier 126 (Analog Devices Part No. OP213ES) that receives the chosen reference voltage signal at its negative input. Operational amplifier 126 is connected to act as a voltage comparator, such that when the pressure ramp voltage signal associated with pressure sensor 60 reaches the chosen threshold reference voltage, the output voltage of operational amplifier 126 goes to VDD. The output signal is then applied to a lamp driver 128 (Philips Semiconductor Part No. BUK581-60A) connected along line 150 to emitters 70. Lamp driver 128 is timed to provide a very brief emission pulse from emitters 70 on the order of 50 micro-seconds. This pulse can be considered a "pseudo-applanation event" in that it simulates applanation by causing the applanation detection system of NCT 12 to detect a well-defined peak corresponding to applanation as though a human eye were being tested.

Below is a table of values for the resistors and capacitors in the controller circuit of FIG. 10.

| R1 | 680 Ω | R15 | 1 kΩ |
| R2 | 30.1 kΩ | R16 | 4.75 kΩ |
| R3 | 10 kΩ | R17 | 500 Ω |
| R4 | 680 Ω | R18 | 100 Ω |
| R5 | 3.3 kΩ | C1 | .1 μf |
| R6 | 1 MΩ | C2 | .01 μf |
| R7 | 100 kΩ | C3 | 10 μf, 16VDC |
| R8 | 100 Ω | C4 | .1 μf |
| R9 | 1 MΩ | C5 | .01 μf (ROHM MCH215C103KK) |
| R10 | 1 MΩ | C6 | .1 μf |
| R11 | 1.50 kΩ | C7 | 1 μf, 16V |
| R12 | 1 kΩ | C8 | 330 pf |
| R13 | 10 kΩ | C9 | 10 μf, 16VDC |
| R14 | 100 Ω | C10 | .1 μf |

Figure 11:
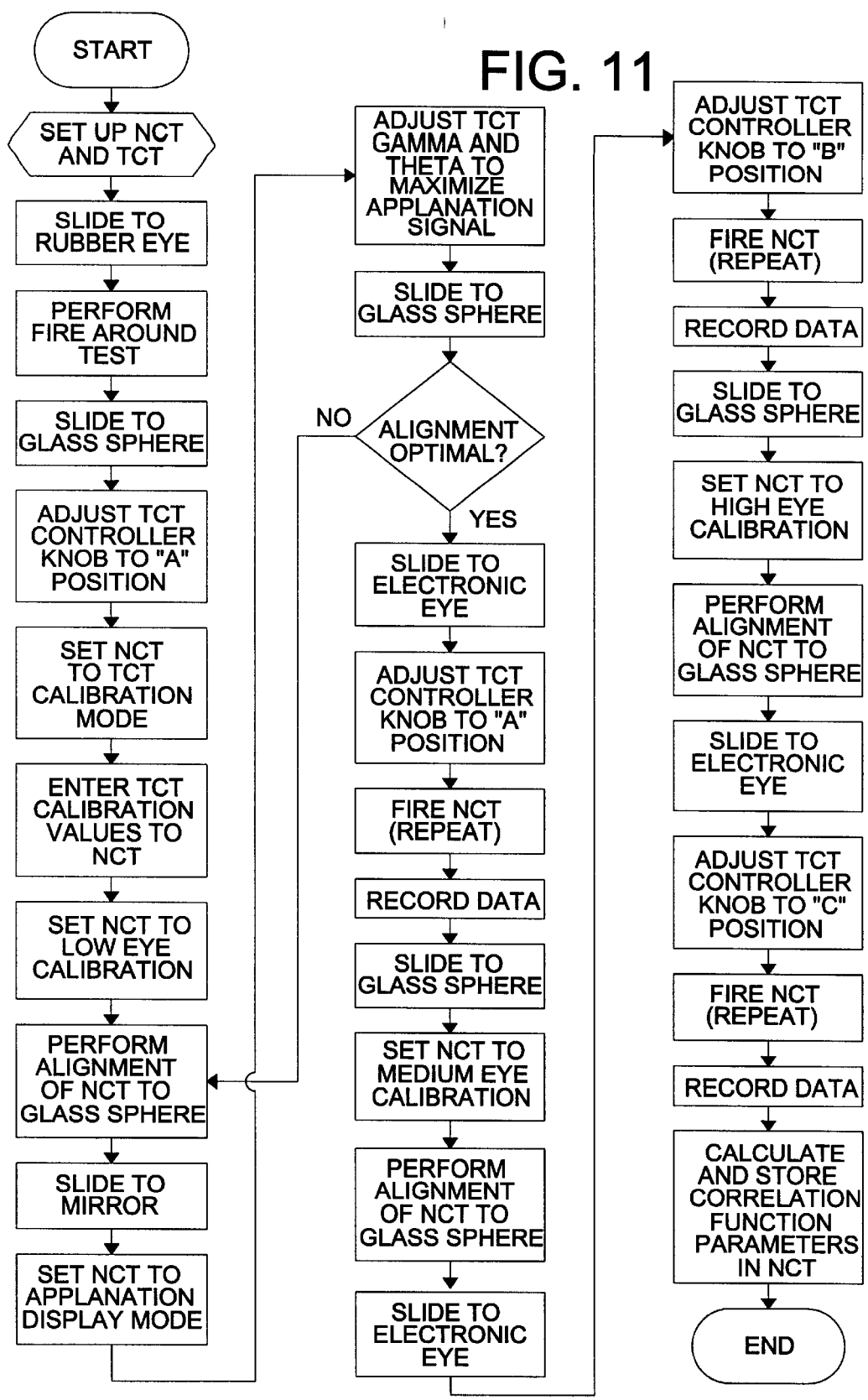
FIG. 11 is a flowchart illustrating a method of calibrating a non-contact tonometer in accordance with the present invention.

FIG. 11 presents a flow chart of a tonometer calibration method employing the tonometer calibration apparatus described above. Once tonometer calibration tool 14 is setup in front of NCT 12, rubber eye 20 is slid into place and a "fire around" test is conducted on the rubber eye to compensate for an offset between an air tube firing axis and a detection optical axis of the instrument, as is well known in the art (a fire around test procedure is preprogrammed into the AT550 NCT available from Reichert Ophthalmic Instruments, a division of Leica Microsystems Inc.). The operator then slides the glass sphere 22 into place and prepares the NCT for calibration. For calibration, the NCT is aligned precisely to glass sphere, mirror 26 is slid into place, and the NCT is set to an applanation display mode. When NCT 12 is in this mode, the operator may adjust the tilt (gamma) and swivel (theta) angular adjustments of the tonometer calibration tool such that light is reflected from mirror 26 to provide an optimal applanation signal. The alignment and angular orientation adjustments are preferably repeated one or more time until the operator is confident that optimal overall alignment has been achieved. At this point, the electronic eye 24 is slid into place in front of air tube 11, the selector knob 84 of controller 18 is set to the "A" position corresponding to a low IOP, and the NCT is fired repeatedly. The electronic eye reacts by generating a pseudo-applanation event when a gain-adjusted pressure signal from pressure sensor 60 reaches a threshold level associated with the "A" position of selector switch 116. The IOP measurement data from the repeated firings is recorded. The alignment, firing, and recording procedures are repeated for the "B" and "C" selector knob positions corresponding to a medium IOP and a high IOP, respectively.

It is assumed that tonometer calibration tool 14 itself has been calibrated, and contains calibration values on a certificate of calibration that are preferably also recorded in spaces 94A, 94B, and 94C on the controller housing. To achieve calibration, it is necessary to obtain agreement, within an acceptable tolerance, of the A, B, and C readings from NCT 12 with the corresponding calibration values for the tonometer calibration tool. Therefore, the parameters of a correlation function stored by NCT 12 must be recalculated and stored based on the NCT measurement data. For example, where NCT employs a quadratic correlation function $ax^2+bx+c$ where x is a measurement voltage indicative of the plenum pressure, the a, b, and c parameters are adjusted and stored to provide a best fit. By way of further example, where NCT 12 employs a linear correlation function, the slope and Y-intercept (offset) of the linear function are adjusted to achieve a best fit.

Figure 12:
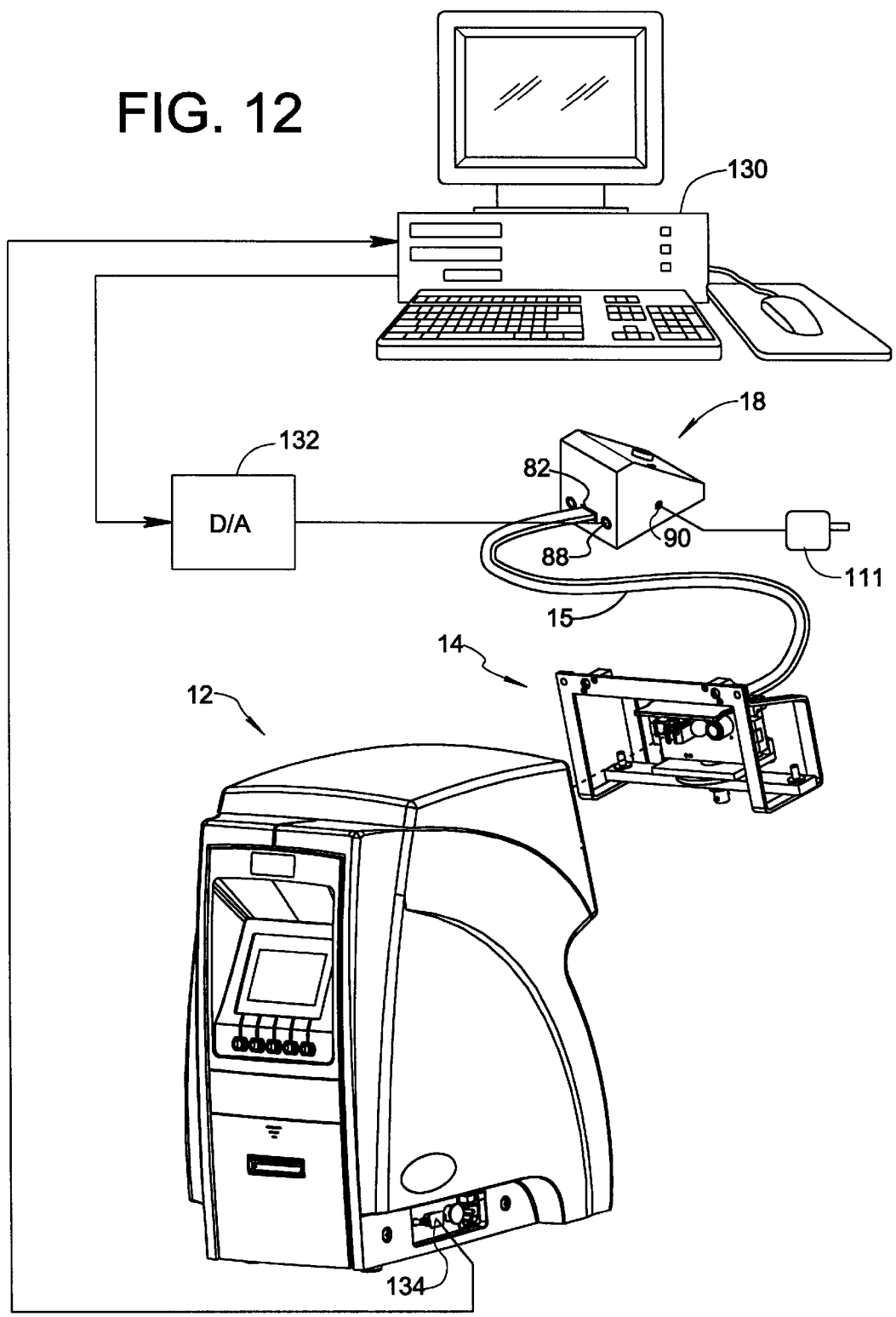
FIG. 12 is a schematic diagram illustrating an alternative system configuration for calibrating a non-contact tonometer in accordance with the present invention.

FIG. 12 shows an alternative calibration system arrangement wherein an external device provides a custom threshold voltage when selector knob 84 is set to the "EXT." position. In this example arrangement, a computer 130 feeding a digital signal to a digital-to analog signal converter 132 establishes the voltage threshold of controller 18 (shown with an associated power adapter 111). Computer 130 is connected to a serial data port 134 of NCT 12 to directly receive measurement data from the NCT. In this arrangement, an operator can easily customize a calibration procedure.

Figure 13:
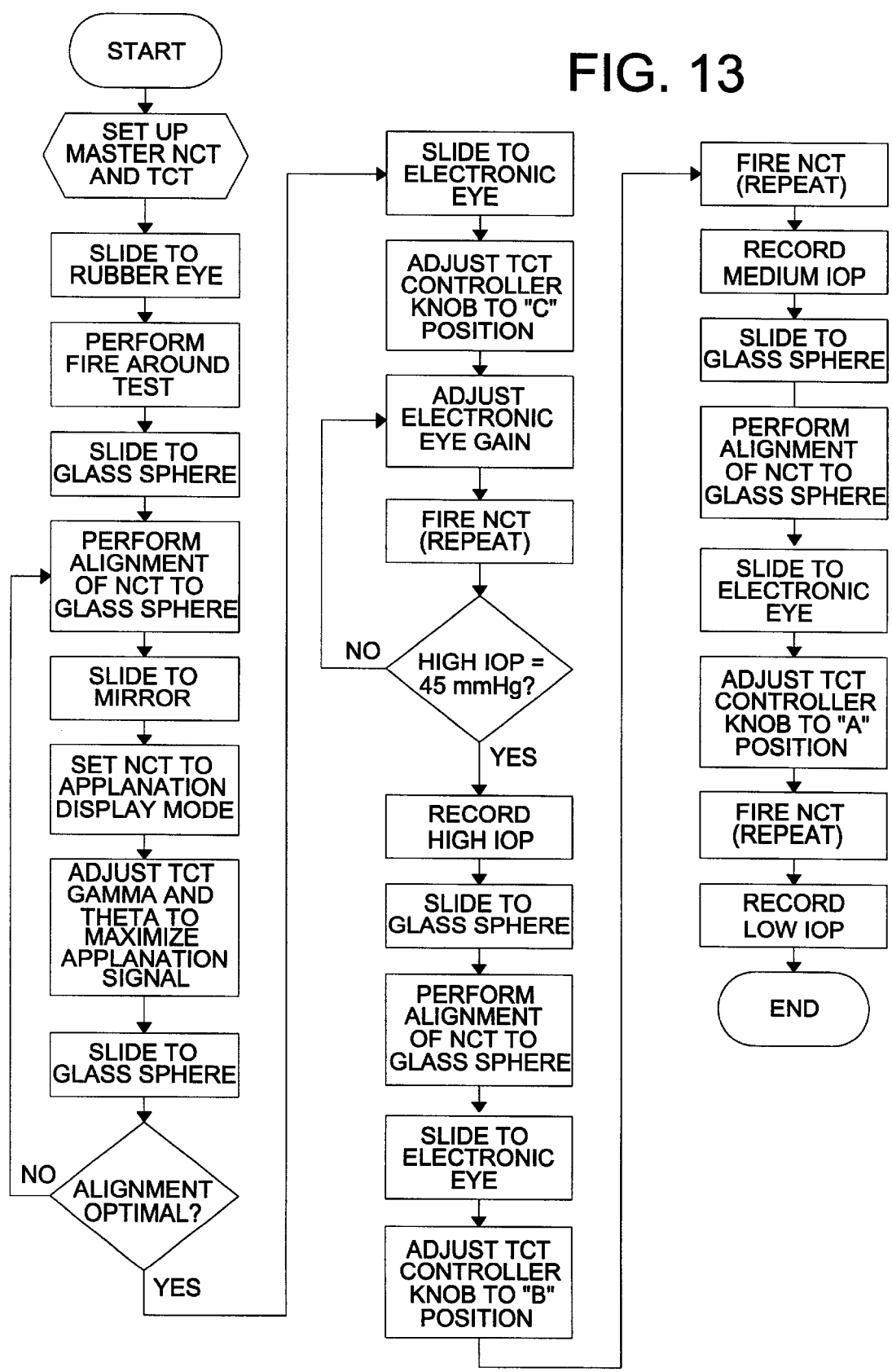
FIG. 13 is a flowchart illustrating a method of calibrating a tonometer calibration tool of the present invention.

As alluded to above with respect to FIG. 11, tonometer calibration tool 14 must itself be calibrated against a known IOP measurement standard. A procedure for this is illustrated in the flowchart of FIG. 13. The procedure involves setting up and aligning the tonometer calibration tool opposite calibrated NCT, such as a master NCT clinically calibrated against a Goldmann Applanation Tonometer (GAT). A high IOP calibration value is established by setting selector knob 84 to the "C" position, firing the NCT, and adjusting potentiometer 110 to adjust the pressure signal gain until the NCT gives an accepted high IOP reading such as 45 mmHg. Medium and low calibration values for the particular gain setting are then established by turning the selector knob to the appropriate setting, firing the master NCT, and recording an average IOP value. The high, medium, and low IOP calibration values can then be recorded in spaces 94C, 94B, and 94A, respectively.

Figure 14:
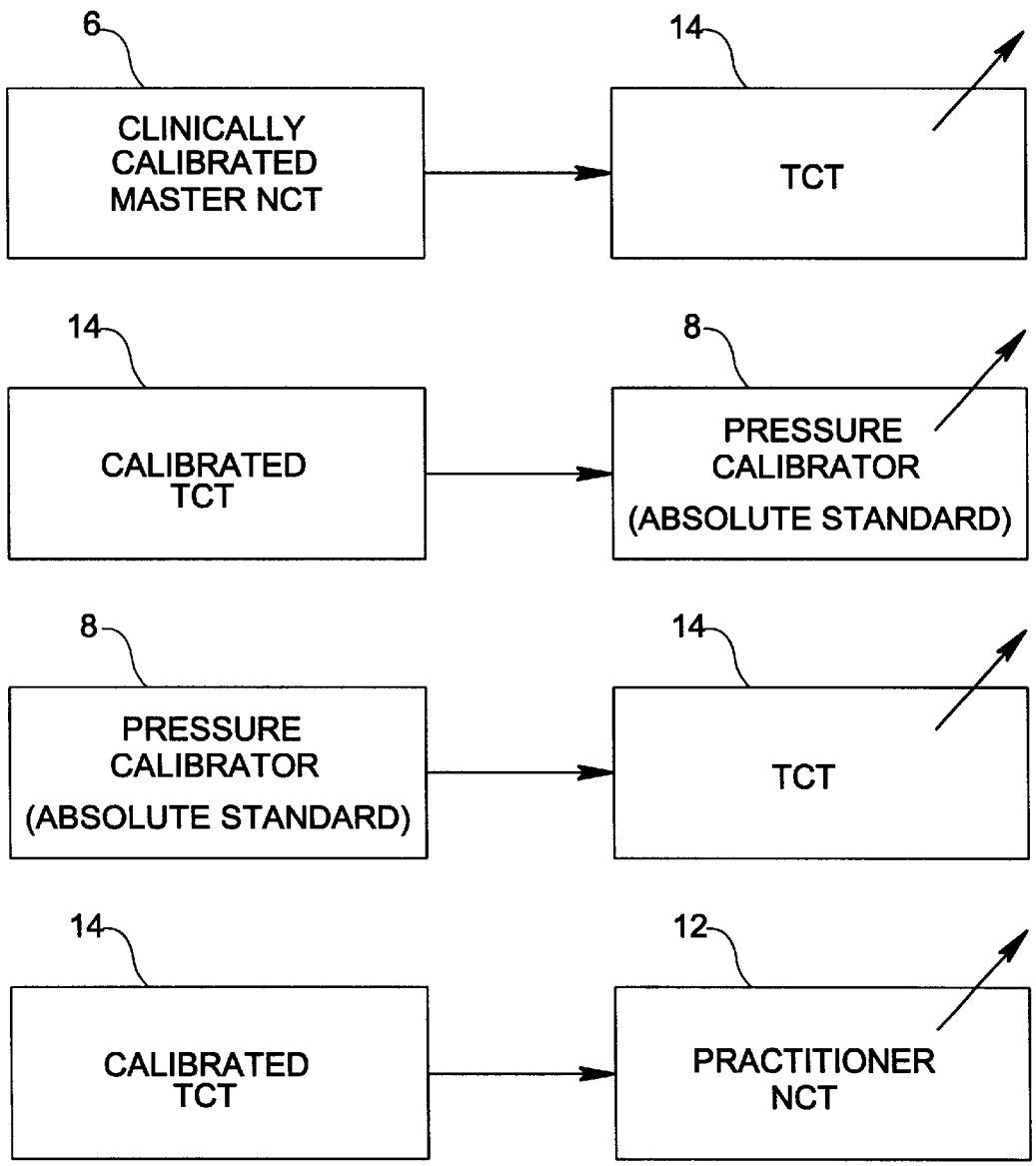
FIG. 14 is a block diagram schematically illustrating use of an absolute calibration standard for calibrating a tonometer calibration tool of the present invention.

As will be appreciated from FIG. 14, a pressure calibrator 8, or other absolute pressure standard such as a column of fluid, can be adjusted against a tonometer calibration tool that has been calibrated against a clinically calibrated master NCT 6, and then used to calibrate other tonometer calibration tools, which are then used to calibrate practitioner NCTs in the field. Thus, the present invention reduces the need for expensive clinical calibrations by providing a calibration that is traceable to an absolute standard.

What is claimed is:

1. An apparatus for calibrating a non-contact tonometer of a type operable to measure intraocular pressure (IOP) of an eye by discharging an air pulse at said eye to applanate a cornea of said eye, said apparatus comprising:
   a pressure sensor for receiving said air pulse, said pressure sensor providing a pressure signal in response to said air pulse; and
   applanation simulation means connected to said pressure sensor for providing a pseudo-applanation event when said pressure signal reaches a predetermined level corresponding to a known IOP measurement standard, said pseudo-applanation event being detected by said non-contact tonometer as though an actual corneal applanation had taken place.

2. The apparatus according to claim 1, further comprising a controller having means for adjusting said predetermined level.

3. The apparatus according to claim 2, wherein said means for adjusting said predetermined level includes a selector switch for choosing one of a plurality of predetermined levels.

4. The apparatus according to claim 3, wherein said controller includes an input jack for connecting an external calibration source to said controller, and one of said plurality of predetermined levels corresponds to a signal from said external calibration source.

5. The apparatus according to claim 1, further comprising means connected to said pressure sensor for adjusting the gain of said pressure signal.

6. The apparatus according to claim 1, wherein said pressure sensor comprises a piezoresistive semiconductor sensing element.

7. The apparatus according to claim 6, wherein said sensing element is covered by a polymer for reducing flow noise in said pressure signal.

8. The apparatus according to claim 6, wherein said pressure sensor is temperature compensated.

9. The apparatus according to claim 1, wherein said applanation simulation means comprises at least one radiation emitter driven to emit a pulse of radiation as said pseudo-applanation event.

10. The apparatus according to claim 9, wherein said pulse of radiation is about 50 micro-seconds in duration.

11. The apparatus according to claim 9, wherein said at least one radiation emitter includes a pair of radiation emitters located on opposite sides of said pressure sensor.

12. The apparatus according to claim 11, wherein said pressure sensor and said pair of radiation emitters are fixed to a unitary holder.

13. The apparatus according to claim 1, further comprising a glass sphere for use in aligning said non-contact tonometer relative to said pressure sensor.

14. The apparatus according to claim 13, wherein said pressure sensor and said glass sphere are mounted on a slide mechanism having detent stops at locations respectively corresponding to said pressure sensor and said glass sphere.

15. The apparatus according to claim 13, further comprising a planar reflection surface for use in angularly orientating said pressure sensor relative to said non-contact tonometer.

16. The apparatus according to claim 15, wherein said pressure sensor, said glass sphere, and said reflection surface are mounted on a slide mechanism having detent stops at locations respectively corresponding to said pressure sensor, said glass sphere, and said reflection surface.

17. The apparatus according to claim 16, wherein said slide mechanism includes a front plate to which said pressure sensor, said glass sphere, and said reflection surface are fixed; a slider fixed to said front plate; a middle plate parallel to said front plate; a linear slider track fixed to said middle plate for slidably receiving and guiding said slider; a rear plate parallel to said middle plate; a base plate fixed to said rear plate; a pivotal connection between said middle plate and said rear plate for permitting said middle plate to be tilted relative to said base plate about a tilt axis; a tilt adjustment screw extending through said rear plate and operatively connected to said middle plate for adjusting a tilt angle of said middle plate about said tilt axis; a swivel platform having a swivel shaft defining a swivel axis and at least one arcuate slot about said swivel shaft, said base plate being supported by said swivel platform to permit rotation about said swivel axis; and at least one swivel set screw extending through said at least one arcuate slot in said swivel platform and coupled to said base plate for clamping said base plate to said swivel platform at a chosen swivel angle about said swivel axis.

18. The apparatus according to claim 15, further comprising a rubber eye for use in compensating for an offset between a test axis and an optical axis of said non-contact tonometer.

19. The apparatus according to claim 18, wherein said pressure sensor, said glass sphere, said reflection surface, and said rubber eye are mounted on a slide mechanism having detent stops at locations respectively corresponding to said pressure sensor, said glass sphere, said reflection surface, and said rubber eye.

20. A calibration system comprising, in combination:
   a non-contact tonometer operable to measure intraocular pressure (IOP) of an eye by discharging an air pulse at said eye to applanate a cornea of said eye;
   a tonometer calibration tool comprising a pressure sensor for receiving said air pulse and providing a pressure signal in response to said air pulse and an applanation simulation means for providing a pseudo-applanation event;
   a controller connecting said applanation simulation means to said pressure sensor such that said pseudo-applanation event occurs when said pressure signal reaches a predetermined level corresponding to a known IOP measurement standard, said pseudo-applanation event being detected by said non-contact tonometer as though an actual corneal applanation had taken place; and
   a fixture for locating said tonometer calibration tool opposite said non-contact tonometer.

21. The system according to claim 20, wherein said fixture carries said tonometer calibration tool and is mounted on said non-contact tonometer.

22. The system according to claim 21, wherein said controller is remote from said tonometer calibration tool.

23. The system according to claim 20, wherein said tonometer calibration tool further comprises a glass sphere for use in aligning said non-contact tonometer relative to said pressure sensor.

24. The system according to claim 23, wherein said tonometer calibration tool further comprises a planar reflection surface for use in angularly orientating said pressure sensor relative to said non-contact tonometer.

25. A method of calibrating a non-contact tonometer comprising the steps of:
   A) operating said non-contact tonometer to direct an air pulse onto a pressure sensor;
   B) comparing a pressure signal from said pressure sensor with a predetermined signal level corresponding to a known IOP measurement standard;
   C) inducing said non-contact tonometer to detect applanation when said pressure ramp signal from said pressure sensor reaches said predetermined signal level such that said non-contact tonometer provides a measured pressure value; and
   D) adjusting at least one parameter of a correlation function of said non-contact tonometer to reduce a difference between said measured pressure value and said known IOP measurement standard.

26. The method according to claim 25, wherein said steps (A) through (C) are performed using a plurality of different known IOP measurement standards to provide a corresponding plurality of said measured pressure values, and said correlation function is adjusted based on said plurality of IOP measurement standards and said corresponding plurality of measured pressure values.

27. The method according to claim 26, wherein said plurality of different known IOP measurement standards includes a low IOP measurement standard, a medium IOP measurement standard, and a high IOP measurement standard.

28. The method according to claim 25, wherein said known IOP measurement standard is traceable to a clinically calibrated non-contact tonometer.

29. The method according to claim 28, wherein said clinically calibrated non-contact tonometer is calibrated against a Goldmann Applanation Tonometer.

30. The method according to claim 25, wherein said known IOP measurement standard is traceable to an absolute pressure standard.

31. The method according to claim 30, wherein said absolute pressure standard is provided by a pressure calibrator.

32. The method according to claim 30, wherein said absolute pressure standard is provided by a fluid column.

* * * * *